(12) United States Patent
Morini et al.

(10) Patent No.: US 7,067,690 B2
(45) Date of Patent: Jun. 27, 2006

(54) SEPARATION OF DIASTEREOISOMERS

(75) Inventors: Giampiero Morini, Padua (IT); Fabrizio Piemontesi, Ferrara (IT); Antonio Cristofori, S. M. Maddalena (IT); Stefania Milani, Romano d'Ezzelino (IT)

(73) Assignee: Basell Poliolefine Italia S.p.A., Milan (IT)

( * ) Notice: Subject to any disclaimer, the term of this patent is extended or adjusted under 35 U.S.C. 154(b) by 165 days.

(21) Appl. No.: 10/499,273

(22) PCT Filed: Dec. 20, 2002

(86) PCT No.: PCT/EP02/14875

§ 371 (c)(1),
(2), (4) Date: Jun. 18, 2004

(87) PCT Pub. No.: WO03/055831

PCT Pub. Date: Jul. 10, 2003

(65) Prior Publication Data

US 2005/0171379 A1    Aug. 4, 2005

(30) Foreign Application Priority Data

Dec. 24, 2001 (EP) ................. 01205252

(51) Int. Cl.
*C07C 69/34* (2006.01)
(52) U.S. Cl. ............. 560/190; 560/191; 568/672; 568/682
(58) Field of Classification Search ........... 560/190, 560/191; 568/672, 682
See application file for complete search history.

(56) References Cited

FOREIGN PATENT DOCUMENTS

| GB | 1216190 | 12/1990 |
|---|---|---|
| WO | 9832727 | 7/1998 |
| WO | 0011057 | 3/2000 |

OTHER PUBLICATIONS

G. W. Wheland, "Chapter 8. The Stereochemistry of Carbon;" *Advanced Organic Chemistry*; John Wiley & Sons, Inc., Third Edition, p. 306-319 (1960).
E. E. Eliel, "4-4. Resolution of Racemic Modifications;" *Stereochemistry of Carbon Compounds*; McGraw-Hill Book Company, Inc.; p. 47-86 (1962).
F. G. Bordwell, "§17.6 Diastereomers and Resolution;" *Organic Chemistry*; The Macmillan Company; p. 612-618 (1963).
I. S. Krull, "Chapter 6. The Liquid-Chromatographic Resolution of Enantiomers;" *Advances in Chromatography*; vol. 16, p. 175-210 (1978).
Y. Matsumura et al.; "Dependence of the Reactivities of Titanium Enolates on How They Are Generated: Diastereoselective Coupling of Phenylacetic Acid Esters Using Titanium Tetrachloride;" *J. Org. Chem.*, vol. 61(8), p. 2809-2812 (1996).

*Primary Examiner*—Samuel Barts
(74) *Attorney, Agent, or Firm*—Jarrod N. Raphael; William R. Reid

(57) ABSTRACT

Process for modifying the relative ratios of the components of a liquid starting mixture of specific diastereoisomers, containing at least two asymmetric carbon atoms comprising contacting said liquid mixture with a Lewis acid compound capable of co-ordinating a compound having at least two Lewis basic functionalities and subjecting the resulting mixture to conditions such that a reaction product, having a molar ratio between its diastereoisomeric components different from the corresponding molar ratio in the said liquid starting mixture, becomes separated from the said liquid mixture, said process being carried out using an amount of said Lewis acid not enough to co-ordinate the total amount of the diastereoisomeric components of the liquid starting mixture.

This method shows an excellent balance of efficiency and easiness of procedure that cannot be reached with the physical methods of diastereoisomers separation known in the art.

12 Claims, No Drawings

SEPARATION OF DIASTEREOISOMERS

This application is the U.S. national stage of International Application PCT/EP02/14875, filed Dec. 20, 2002.

The present invention relates to a method for modifying the relative ratios of the components of a mixture of diastereoisomers. In particular, the present invention relates to a process for increasing the content of at least one diastereoisomeric component of a staring mixture of diastereoisomers. The separation of diastereoisomers is a problem that is frequently faced in the scientific field. Due to the difference in the properties of the diastereoisomers, it is very often necessary trying to separate from a diastereoisomeric mixture at least one of the diastereoisomers as pure as possible. The methods commonly used in the art are of physical type and they are based on the difference in the properties of diastereoisomers such as boiling point, melting point, solubility, etc. E. L. Eliel in "Stereochemistry of carbon compounds" (McGraw-Hill, 1962, pp. 49–85) reports that, among the many different physical methods of separation of mixtures, fractional distillation, chromatography and fractional crystallisation are the most useful as regard diastereoisomers. It is customary to use fractional crystallisation as it is said by F. G. Bordwell in "Organic chemistry" (The Macmillan Company, 1963, pp. 616–618), but dozens of crystallisation steps may be required. Furthermore, certain complications may arise which make the above procedure inapplicable, as explained by G. W. Wheland in "Advanced organic chemistry" (John Wiley & Sons, 3rd ed. 1960, pp. 306–319). In fact, the mixture of diastereoisomers may be an uncrystallisable syrup or oil; or it may be an inseparable solid solution or compound. Also the solubility of the diastereoisomers may be so similar in all solvents that the desired separation is difficult. Finally, although the less soluble diastereoisomer can be precipitated from the solution in a satisfactorily pure state, the more soluble one, when recovered from the mother liquor, is always contaminated with the other stereoisomer. Consequently, this method seldom permits the isolation of the single diastereoisomers of a mixture in a pure state. When chromatography, in particular column chromatography, is used for the separation of diastereoisomers (I. S. Krull "Advances in chromatography", vol. 16, Marcel Dekker, 1978, pp. 175–183) it is possible to separate in some cases the racemic from the meso stereoisomers with a yield not superior to about 80% (Y. Matsusmura, M. Nishimura, H. Hiu, M. watanabe, N. Kise, *J. Org. Chem.*, 1996, 61, 2809–2812). Also, even if chromatography is fast becoming the method of choice for the separation of large amounts of diastereoisomers, it is necessary to work out the best separation conditions, the best packing material, solvent conditions, flow rate, column size, temperature and other factors. All of this requires a good deal of time, equipment, solvents, etc. The above mentioned methods are all based on the intrinsic properties of the molecules of diastereoisomers to be separated (b.p., m.p., solubility, etc.) and are as much effective as the said properties of the diastereoisomeric components of the starting mixture are different.

Furthermore, the separation obtained with the physical methods described previously is not very efficient in term of purity and yield and involves a relevant number of steps in order to achieve the expected result. The applicant has now found a new process showing an excellent balance of efficiency and easiness of procedure that cannot be reached with the physical methods of separation known in the art. An object of the present invention is a method for modifying the relative ratios of the components of a liquid starting mixture of diastereoisomers of formula (I) in which the diastereoisomers have at least two asymmetric carbon atoms, n is an integer from 0 to 2, $R_1$, $R_2$, $R_3$ and $R_4$, same or different to each other, are H or $C_1$–$C_{20}$ hydrocarbon groups, optionally containing heteroatoms, G is a —COOR', —OR', —C=OR', —NR$_2$', or —PR$_2$' group, with R' having the same meaning as $R_1$–$R_4$, which comprises the following steps:

(i) contacting said liquid mixture with a Lewis acid compound, capable of co-ordinating at least one component of the starting mixture, which is used in an amount not enough to co-ordinate the total amount of the diastereoisomeric components of the liquid starting mixture, and (ii) subjecting the resulting mixture to conditions such that a reaction product, having a molar ratio between its diastereoisomeric components different from the molar ratio in which they were present in the said liquid starting mixture, becomes separated from the said liquid mixture.

Without wanting to be bound by any theory, one of the possible explanations for the effectiveness of the present invention may be found in the different capability of the diastereoisomers of formula (I) of co-ordinating a Lewis acid compound. Particularly suitable in carrying out the present invention are the Lewis acid compounds of formula $MX_z$, in which M is a metal or a transition metal belonging to the Group 1–16 (new notation) of the Periodic Table of the Elements, z represents the valence of the element M and X is a halogen. Among the metals and the transition metals, Mg, Ca, Zr, Fe, Ni and Ti are the preferred ones. Mg and Ti are particularly preferred. X is preferably chlorine. Specific Lewis acid compounds useful for the process of the present invention are $TiCl_4$, $ZrCl_4$, $MgCl_2$, $NiCl_2$, $FeCl_3$. In a particular embodiment of the present invention the Lewis acid is used in liquid form. This can be done either by using a Lewis acid that is already liquid at room temperature or by dissolving said Lewis acid in suitable non-coordinating solvent such as liquid hydrocarbons or halogenated hydrocarbons. In a particular embodiment of the present invention the diastereoisomers of formula (I) have the asymmetric carbon atoms linked at the G groups described above. In particular, the diastereoisomers of formula (I) can be suitably selected from those in which G is a —COOR' or —OR' group and n is 0 or 1. In the same embodiment, $R_1$ is preferably a hydrogen atom, $R_2$ is preferably a $C_1$–$C_6$ alkyl or cycloalkyl radical, $R_3$ is preferably hydrogen, $R_4$ is preferably hydrogen or a methyl moiety and R' is preferably a $C_1$–$C_4$ alkyl radical. When G is a —COOR' group and n is 0, $R_1$ is preferably hydrogen, $R_2$ is preferably selected from the group consisting of methyl, i-propyl, sec-butyl, t-butyl and cyclohexyl; R' is preferably selected from the group consisting of methyl, ethyl and i-butyl. In another particular embodiment of the present invention, the mixture to be separated comprises the described compounds of formula (I) in their rac and meso conformation in variable molar amounts. Particularly preferred are the diastereoisomeric mixtures of the following compounds: diethyl-2,3-di-i-propyl-succinate, di-i-butyl-2,3-di-i-propyl-succinate, diethyl-2,3-di-cyclohexyl-succinate, diethyl-2,3-di-t-butyl-succinate, diethyl-2,3-di-sec-butyl-succinate, dimethyl-2,4-di-methyl-glutarate, and 2,3-di-i-propyl-1,4-dimethoxybutane. According to the present invention the diastereoisomeric compounds of formula (I) are present in the liquid starting mixture. This can be obtained for example by contacting the compounds of formula (I) with an appropriate inert solvent. Examples of suitable solvents can be aliphatic hydrocarbons like pentane, hexane, heptane or their mixtures or aromatic hydrocarbons as benzene, toluene, xylene or their mixtures. Also halogenated hydrocarbon solvents can be used like chloroform, chlorobenzene, dichloromethane or their mixtures.

As already explained, the process is carried out by adding to the liquid mixture of diastereoisomers described above the Lewis acid compound. The addition of the Lewis acid can be carried out in a controlled manner. For example, a liquid Lewis acid can be dripped into the liquid mixture, while a solid Lewis acid can be added in small amounts, stirring the said liquid mixture after every addition. The above described contact of the liquid mixture with the Lewis acid is suitably carried out in an inert atmosphere. According to the present invention, during or after the addition of the Lewis acid the system is subject to conditions under which a reaction product becomes separated from the liquid starting mixture. In a particular aspect of the present invention, the conditions under which the reaction product becomes separated are the same as those under which the Lewis acid addition is carried out. In this case, the separation of the reaction product readily occurs during the addition of the Lewis acid. This situation can occur when the Lewis acid is a solid insoluble in the reaction system (and the reaction product is insoluble as well) or when the product of the reaction between the Lewis acid and the compound of formula (I) is insoluble under the conditions that, instead, allow the compound of formula (I) to be in solution. If upon the addition of the Lewis acid compound, the reaction product does not separate, it is necessary to modify the conditions to obtain the said separation. The modification of the conditions can be done in accordance with the general principles controlling the solubility of a compound in a solvent. Thus, as an example, variations in terms of temperature, solution, solvent, etc., can give rise to a separation of the reaction product from the liquid starting mixture. It has been experienced by the applicant that the separation is more easily achieved working with concentrated solutions. In particular, concentrations in the range of 0.5–2M can suitably be used. As explained above, in order to achieve the results described in the present invention, the amount of the Lewis acid added to the mixture must be lower than the amount that is necessary to co-ordinate all the diastereoisomers present in the liquid mixture. When suitable, the Lewis acid compound can be added to the starting mixture in a quantity enough to co-ordinate substantially all the amount of only one of the diastereoisomeric components of the mentioned mixture. As an example, when the mixture is constituted of only two diastereoisomers, rac and meso respectively that react according to the following scheme (1):

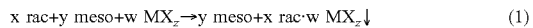

$$x\ rac + y\ meso + w\ MX_z \rightarrow y\ meso + x\ rac \cdot w\ MX_z \downarrow \qquad (1)$$

it is preferred that the amount w of the Lewis acid is not enough to react also with the meso diastereoisomer.

In view of the above, it is important to know the co-ordination capability of the Lewis acid in order to be able to add the right amount of said acid to fully achieve the advantages from of the present invention. Said determination, even if it may be in some cases rather long, does not involve technical difficulties to be overcome and can be carried out by the person skilled in the art as a routine procedure. Here below are reported the guidelines for performing the said determination. In accordance with the present invention the amount of Lewis acid not enough to co-ordinate all the diastereoisomers of the starting liquid mixture is a molar amount lower than the number obtained by applying the formula X·(A/D) where X is the total amount in moles of the diastereoisomers present in the liquid starting mixture and (A/D) is the value of the molar ratio between said Lewis acid (A) and the diastereoisomers (D) in the separated reaction product. In some cases the co-ordination capability of a Lewis acid with respect to a certain group of basis can be already known or derivable on the basis of what is reported in the scientific literature, textbook etc. In some other cases, the co-ordination capability with respect to a specific compound of formula (I) should be determined. The applicant observed that in many cases the Lewis acids that are liquid or soluble in non co-ordinating solvents at room temperature react with the diastereoisomers of formula (I) forming reaction products in which the molar ratio (A/D) is 1. In such cases, following the above reported formula, the amount of the Lewis acid to be added is simply lower than the total molar amount of the diastereoisomers in the liquid starting mixture. As explained above, when only one diastereoisomer is found in the separated reaction product, an high efficiency of separation is obtainable by adding a molar amount of the Lewis acid substantially equal to the molar amount of the diastereoisomer present in the reaction product. There could be cases in which in the reaction product that is separated the molar ratio A/D is lower than 1, such as 0.5 or lower. As said before, in such cases, the amount of Lewis acid not enough to co-ordinate all the diastereoisomers of the starting liquid mixture will be easily determined by applying the above-reported formula. As a practical advice, in order to verify the A/D ratio of the reaction product, it is suggested to carry out a small-scale separation trial. For example, a small amount (preferably in large defect in order to be reasonably sure to avoid separation of all the diastereoisomers) of the Lewis acid can be added to the mixture to be separated in order to cause the separation of the reaction product. Such reaction product is then analysed for the determination of the A/D ratio. Once the determination has been carried out, the experiment can be repeated under the same conditions but on a larger scale with the use of the proper amount of the Lewis acid. If the Lewis acid is a solid compound insoluble under the reaction conditions, its co-ordination capability may be a function of several factors such as granulometry, surface area, porosity, etc. In this event, the co-ordination capability can be determined via a small scale experiment carried out by adding subsequent known small amounts of the starting mixture to the solid Lewis acid (used in excess) and analysing, after each addition, the liquid phase to check for the presence of the diastereoisomers. It is advisable to carry out this experiment by adding small amounts of liquid mixture. The applicant found profitable to carry out successive additions of the starting mixture containing an amount of diastereoisomer of about 5% molar with respect to the moles of the metal M of the Lewis acid. As soon as one or more diastereoisomers are found in the liquid phase and their amount detected, it will be known in that conditions the maximum co-ordination capability of the Lewis acid for the diastereoisomer(s) found in the liquid phase and the corresponding molar ratio A/D of the reaction product. Once the molar ratio A/D has been determined, the molar amount of Lewis acid to be used can be calculated according to the formula disclosed above. The accurate determination of the A/D ratio can provide useful information for an efficient use of the process of the invention especially in case in which the Lewis acid is a solid compound insoluble under the reaction conditions. As an example we can describe the case in which a mixture of two diastereoisomers (D1 and D2) in equimolar ratio has to be separated by the use of a Lewis acid having and higher affinity for D2. By following the procedure disclosed above in order to determine the A/D ratio, it will happen that after a certain addition of the liquid starting mixture only D1 will be found in the liquid phase. At this point it can be assumed that the maximum co-ordination capability of the Lewis acid has been reached for D1 only, while the Lewis acid will have a still remaining co-ordination capability for D2. Thus, it will be possible to calculate the $A/D_1$ ratio (in which $D_1$ is the molar amount of D1 in the solid reaction product). By keep adding small amounts of liquid starting mixture also $D_2$ will be found in the liquid phase. At this point it will be possible to determine also the ratios $A/D_2$ (in which $D_2$ is the molar amount of D2 in the solid reaction product) and $A/D_T$ (in which $D_T$ is the total molar amount, in the solid reaction product, of the diastereoisomers D1 and D2) The relationship between the various ratios will be:

$$A/D_1 > A/D_2 > A/D_T.$$

Once these parameters have been identified the skilled in the art has available several choices for carrying out the process of the present invention. The large scale process can for example be carried out using a molar amount of the Lewis acid lower than that obtainable with the formula $X \cdot (A/D_T)$, where X is the total amount in moles of the diastereoisomers present in the liquid starting mixture and $A/D_T$ has the meaning given above, thereby obtaining a solid reaction product in which the relative content of D2 is increased with respect to its content in the liquid starting mixture, and a liquid phase in which substantially only D1 is contained. However, a higher efficiency of separation (in terms of a higher amount of D1 in the liquid phase and consequently a higher content of D2 in the solid reaction product) can be obtained by carrying out the process using a molar amount of the Lewis acid lower than or preferably equal to that obtainable with the formula $X_2(A/D_2)$, where $X_2$ is the molar amount of D2 in the liquid starting mixture and $A/D_2$ has the meaning given above.

Turning to the general aspects of the invention, it is important to emphasise that the co-ordination capability of the Lewis acid is always related to the reaction conditions of the small-scale experiment. Therefore, in order to surely obtain the object of the present invention, the separation conditions used in the small-scale experiment should also be applied at the large-scale process. By performing the said small scale experiment, it may occur that all the solid Lewis acid become dissolved before the presence in the liquid phase of any of the diastereoisomer(s) is detected. In such case, it is necessary to apply the known methods of the art (variation of temperature, solvent, distillation, evaporation, etc.) in order to precipitate a solid reaction product separated from the mixture. Once the solid has been obtained, the molar ratio A/D can be determined on it. In this situation, the large scale process can be carried out under the conditions which caused the precipitation of the solid reaction product in the small scale experiment, adding at the liquid starting mixture a molar amount of Lewis acid lower than $X \cdot (A/D)$ where X, A and D have the meaning given above. As explained at the end of the process of the present invention, there will be one or more diastereoisomers in the liquid phase and in the solid reaction product as well. In all cases the relative ratios between them will be different from the original ratio in the liquid starting mixture. The diastereoisomers in the liquid phase can be recovered simply by removing the solvent according the appropriate technique known in the art. In many cases the removal is obtained by heating the solution under atmospheric pressure or lower. Diastereoisomers that are subject to decomposition by virtue of high temperature can be isolated by removing the solvent at low temperatures under vacuum. The recovery of the diastereoisomer(s) contained in the solid reaction product can be obtained by decomposing the solid reaction product through a chemical reaction. This kind of method is very well known in the art and is often based on the use of a compound that is capable to displace the diastereisomer from the Lewis acid in view of an higher affinity for the said Lewis acid. As an example, when $TiCl_4$ or $MgCl_2$ are used as Lewis acid according to the present invention and the compound of formula (I) is an ester, the solid reaction product is decomposed by reacting it with water in an acid environment. The ester can then be recovered by extracting the aqueous phase with a liquid which is a solvent for the ester and at the same time immiscible with water.

The following examples are given in order to further illustrate and not to limit the invention.

EXAMPLES

Unless otherwise indicated, the percentages in the examples are expressed by weight.

The purity of the stereoisomer is expressed as the weight percentage of the relevant isomer either in the reaction product or in the remaining liquid mixture.

The stereoisomer recovered means the weight percentage of said isomer either in the reaction product or in the remaining liquid mixture in respect of the weight percentage of said isomer in the starting mixture. The temperature reported in Table 1 is the temperature at which the solid/liquid separation is carried out.

Example 1

In a 2 L flask, under nitrogen, 300 mL of toluene and 115.2 g (447 mmol) of diethyl-2,3-di-isopropyl-succinate (racemic/meso=50/50) were introduced and stirred. A solution of 44.5 g (234 mmol) of $TiCl_4$ in 100 mL of toluene was added dropwise at room temperature. The formation of a precipitate is observed during the addition of $TiCl_4$. The mixture was refluxed for 30 minutes and then slowly cooled under mild stirring to 0° C.

The precipitate was separated from the solvent, washed twice with 100 mL of cold (0° C.) toluene, two more times with cold (0° C.) hexane and then dried in vacuum to give 97.9 g of a yellow solid. A sample of this was treated with HCl/water, then extracted in hexane and dried: the $^1H$ NMR revealed the presence of pure diethyl-2,3-di-isopropyl-succinate (racemic/meso=99.1/0.9).

All the toluene solutions were collected and concentrated under nitrogen (725 mL of toluene were distilled off under nitrogen). The solution was cooled to 40° C. and treated with the cold hexane washings giving a yellow precipitate (3.9 g). The solution was treated with water, washed 3 times with water, dried over $Na_2SO_4$ and evaporated to give 56 g of diethyl-2,3-di-isopropyl-succinate (racemic/meso=0.4/99.6).

Example 2

In a 2 L flask, under nitrogen, 1000 mL of hexane and 151.7 g (588 mmol) of diethyl-2,3-di-isopropyl-succinate (racemic/meso=50/50) were introduced and stirred. 52.1 g (274 mmol) of $TiCl_4$ was added dropwise at room temperature. The formation of a precipitate is observed during the addition of TiCl$_4$. The precipitate was separated from the solvent, washed with hexane and then dried in vacuum to give 118 g of a yellow solid. A sample of this was treated with HCl/water, then extracted in hexane and dried: the $^1$H NMR revealed the presence of pure diethyl-2,3-di-isopropyl-succinate (racemic/meso=95.8/4.2).

All the hexane solutions were collected and treated with water, washed 3 times with water, dried over Na$_2$SO$_4$ and evaporated to give 78.8 g of diethyl-2,3-di-isopropyl-succinate(racemic/meso=8.4/91.6).

Examples 3–5

The procedure of Example 1 is used, except that the diastereoisomers mixtures reported in table 1 are used. Also, in said table, are shown the composition of the mixtures, the conditions of separation and the separation results.

Examples 6–8

The procedure of Example 2 is used, except that the diastereoisomers mixtures reported in table 1 are used. Also, in said table, are shown the composition of the mixtures, the conditions of separation and the separation results.

Example 9

In a 2 L flask, under nitrogen, 25 mL of pentane and 2 g (9.9 mmol) of 2,3-di-i-propyl-1,4-dimethoxybutane (racemic/meso=45/55) were introduced and stirred. 0.84 g (4.4 mmol) of TiCl$_4$ was added dropwise at room temperature. The formation of a precipitate is observed during the addition of TiCl$_4$. The solution was refluxed for 30 minutes.

The precipitate was separated from the solvent, washed with pentane and then dried in vacuum to give 1.74 g of a yellow solid. A sample of this was treated with HCl/water, then extracted in hexane and dried: the $^1$H NMR revealed the presence of pure 2,3-di-i-propyl-1,4-dimethoxybutane (racemic/meso=97.3/2.7).

The solution was treated with water, washed 3 times with water, dried over Na$_2$SO$_4$ and evaporated to give 0.92 g of 2,3-di-i-propyl-1,4-dimethoxybutane (racemic/meso=9.2/90.8).

Example 10

At −5° C., 500 mL of di-butyl Magnesium heptane solution (1 M concentration) and 1 L of chlorobenzene were charged in a 2 L flask under inert atmosphere. This solution was treated with anhydrous HCl generated by adding, in 6 hours, 250 mL of HCl (37% wt solution in water) to 500 mL of concentrated H$_2$SO$_4$. The obtained gaseous HCl was carefully dried by bubbling it in two consecutive vessels, each containing 150 mL of concentrated H$_2$SO$_4$ before the addition to the di-butyl Magnesium solution. A white solid is initially formed, then it changed to yellow as soon as the added HCl reached the stoichiometric amount. The immission of HCl was stopped at this point. The solid was collected by filtration, washed several times with hexane and dried under vacuum to give 47 g of product containing nearly 18% wt of residual chlorobenzene.

In a jacketed reactor equipped with a frit on the bottom part, 3.4 g (29 mmol) of MgCl$_2$ (obtained as described above) were suspended in 115 mL of chlorobenzene under nitrogen, stirred and then warmed up to 120° C. A solution containing 15 g of diethyl-2,3-di-isopropyl-succinate (racemic/meso=50/50) in 15 mL of chlorobenzene was added in 7 minutes. The suspension was stirred 1 h at 120° C. and then filtered at the same temperature. The solid was washed twice with 50 mL of chlorobenzene at 120° C. and then 5 times with 50 mL of hexane at 60° C., dried and collected. The solid composition was Mg=12.55% wt, Cl=36.5% wt, diethyl-2,3-di-isopropyl-succinate-44% wt, solvents=0.350% wt).

A sample of this was treated with HCl/water, then, extracted in hexane and dried: the $^1$H NMR revealed the presence of pure diethyl-2,3-di-isopropyl-succinate (racemic/meso=99.1/0.9).

Example 11

The procedure of Example 10 is used, except that the diastereoisomers mixture reported in table 2 is used. Also, in said table, are shown the composition of the mixture, the conditions of separation and the separation results.

Comparative Example

A solution of diethyl 2,3-diisopropylsuccinate (100 g, 57/43 racemic/meso) in hexane (100 mL) was cooled under stirring to −40 C leading to the formation of a white crystalline solid, which was collected, washed with cold (−60 C) hexane (2×25 mL) and dried in vacuo. The solid obtained (23 g) resulted 99.3% pure meso diethyl 2,3-diisopropylsuccinate by NMR. The hexane mother liquors were concentrated in a rotary evaporator to give an oil (77 g) containing 74% of the racemate isomer by NMR.

TABLE 1

| Example | Diastereoisomer | rac/meso | solvent | T (° C.) | Racemic isomer(s) purity (%) | Racemic isomer(s) recovered (%) | meso isomer(s) purity (%) | meso isomer(s) recovered (%) |
|---|---|---|---|---|---|---|---|---|
| 1 | diethyl-2,3-di-i-propyl-succinate | 50/50 | toluene | 0 | 99.1 | 97.8 | 99.6 | 97.2 |
| 2 | diethyl-2,3-di-i-propyl-succinate | 50/50 | hexane | 25 | 95.8 | 85.3 | 91.6 | 93.0 |
| 3 | di-i-butyl-2,3-di-i-propyl-succinate | 39/61 | toluene | −10 | 95.2 | 91.0 | 98.0 | 90.3 |
| 4 | diethyl-2,3-di-cyclohexyl-succinate | 89/11 | toluene | 0 | >99 | 92.3 | 70.0 | n.a. |
| 5 | Dimethyl-2,4-di-methyl-glutarate | 45/55 | toluene | 25 | 98.7 | 86.0 | 99.9 | 96.5 |
| 6 | di-i-butyl-2,3-di-i-propyl-succinate | 41/59 | hexane | 25 | 91.2 | 84.2 | 99.9 | 98.0 |
| 7 | diethyl-2,3-di-cyclohexyl-succinate | 90/10 | hexane | 25 | 98.0 | 94.0 | 98.0 | 85.0 |
| 8 | Diethyl-2,3-di-t-butyl-succinate | 88/12 | hexane | 25 | 96.8 | 94.3 | 98.5 | 90.9 |
| 9 | 2,3-di-i-propyl-1,4-dimethoxybutane | 45/55 | pentane | 25 | 97.3 | 93.0 | 90.8 | 76.0 |

TABLE 2

| Example | Diastereoisomer | Rac/meso | solvent | T (° C.) | racemic isomer(s) purity (%) | racemic isomer(s) recovered (%) | meso isomer(s) purity (%) | meso isomer(s) recovered (%) |
|---|---|---|---|---|---|---|---|---|
| 10 | Diethyl-2,3-di-i-propyl-succinate | 50/50 | chlorobenzene | 120 | 99.5 | 89.4 | n.a. | n.a. |
| 11 | Diethyl-2,3-di-i-propyl-succinate | 50/50 | chlorobenzene | 60 | 99.5 | 86.8 | n.a. | n.a. |

The invention claimed is:

1. A process for modifying the relative ratios of the components of a liquid starting mixture of diastereoisomers of formula (I)

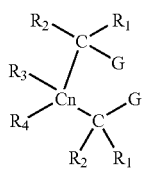

(I)

in which the diastereoisomers have at least two asymmetric carbon atoms, n is an integer from 0 to 2, $R_1$, $R_2$, $R_3$ and $R_4$, same or different to each other, are H or $C_1$–$C_{20}$ hydrocarbon groups, optionally containing heteroatoms, G is a —COOR', —OR', —C=OR', —NR$_2$', or —PR$_2$' group, wherein R' is H or $C_1$–$C_{20}$ hydrocarbon groups, optionally containing heteroatoms, the process comprising the following steps:
   (i) contacting said liquid starting mixture with a Lewis acid compound, capable of co-ordinating at least one component of the starting mixture, which is used in an amount not enough to co-ordinate the total amount of the diastereoisomeric components of the liquid starting mixture; and
   (ii) subjecting the resulting mixture to conditions such that a reaction product, having a molar ratio between its diastereoisomeric components different from the corresponding molar ratio in the said liquid starting mixture, becomes separated from the said liquid mixture.

2. The process according to claim 1 in which the Lewis acid compound has the formula MX$_z$, in which M is a metal or a transition metal belonging to the Group 1–16 (new notation) of the Periodic Table of the Elements, z represents the valence of the element M and X is a halogen.

3. The process according to claim 2 in which M is Mg, Ca, Zr, Fe, Ni or Ti and X is chlorine.

4. The process according to claim 3 in which the Lewis acid is $TiCl_4$, $ZrCl_4$, $MgCl_2$, $NiCl_2$, or $FeCl_3$.

5. The process according to claim 1 in which the diastereoisomers of formula (I) have the asymmetric carbon atoms linked at the G groups.

6. The process according to claim 5 in which G is a —COOR' or —OR' group, n is 0 or 1, $R_1$ is hydrogen, $R_2$ is a $C_1$–$C_6$ alkyl group, $R_3$ is hydrogen, $R_4$ is hydrogen or a methyl moiety and R' is a $C_1$–$C_4$ alkyl radical.

7. The process according to claim 6 in which G is a —COOR' group, n is 0, $R_1$ is hydrogen, $R_2$ is selected from the group consisting of methyl, i-propyl, sec-butyl, t-butyl and cyclohexyl and R' is selected from the group consisting of methyl, ethyl and i-butyl.

8. The process according to claim 1 in which the liquid starting mixture of diastereoisomers of formula (I) comprises diastereoisomers in their rac and meso conformation.

9. The process according to claim 8 in which the liquid starting mixture comprises diastereoisomer mixtures of compounds selected from diethyl-2,3-di-i-propyl-succinate, di-i-butyl-2,3-di-i-propyl-succinate, diethyl-2,3-di-cyclohexyl-succinate, diethyl-2,3-di-t-butyl-succinate, diethyl-2,3-di-sec-butyl-succinate, dimethyl-2,4-di-methyl-glutarate, and 2,3-di-i-propyl-1,4-dimethoxybutane.

10. A process for modifying the relative ratios of the components of a liquid starting mixture of diastereoisomers of formula (I)

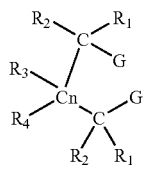

(I)

in which the diastereoisomers have at least two asymmetric carbon atoms, n is an integer from 0 to 2, $R_1$, $R_2$, $R_3$ and $R_4$, same or different to each other, are H or $C_1$–$C_{20}$ hydrocarbon groups, optionally containing heteroatoms, G is a —COOR', —OR', —C=OR', —NR$_2$', or —PR$_2$' group, wherein R' is H or $C_1$–$C_{20}$ hydrocarbon groups, optionally containing heteroatoms, the process comprising the following steps:
   (i) contacting said liquid starting mixture with a Lewis acid compound, capable of co-ordinating at least one component of the starting mixture, which is used in an amount not enough to co-ordinate the total amount of the diastereoisomeric components of the liquid starting mixture; and
   (ii) subjecting the resulting mixture to conditions such that a reaction product, having a molar ratio between its diastereoisomeric components different from the corresponding molar ratio in the said liquid starting mixture, becomes separated from the said liquid mixture;
wherein step (ii) can be carried out during or after step (i).

11. The process according to claim 10 in which the conditions under which the reaction product becomes separated are the same as those under which the Lewis acid addition is carried out.

12. The process according to claim 1 in which the Lewis acid compound can be added to the starting mixture in a quantity enough to co-ordinate substantially all the amount of only one of the diastereoisomeric components of the liquid starting mixture.

* * * * *